(12) United States Patent
Kappus et al.

(10) Patent No.: US 9,987,076 B2
(45) Date of Patent: Jun. 5, 2018

(54) MULTI-FUNCTION SURGICAL INSTRUMENTS

(71) Applicant: COVIDIEN LP, Mansfield, MA (US)

(72) Inventors: John J. Kappus, Denver, CO (US); David N. Heard, Boulder, CO (US); David M. Garrison, Longmont, CO (US); Purvish Soni, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 394 days.

(21) Appl. No.: 14/802,179

(22) Filed: Jul. 17, 2015

(65) Prior Publication Data

US 2016/0074098 A1 Mar. 17, 2016

Related U.S. Application Data

(60) Provisional application No. 62/051,407, filed on Sep. 17, 2014.

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00083* (2013.01); *A61B 2018/1422* (2013.01); *A61B 2018/1467* (2013.01); *A61B 2018/1475* (2013.01)

(58) Field of Classification Search
CPC ............ A61B 18/1442; A61B 18/1445; A61B 18/1447; A61B 2018/1422; A61B 2018/1412; A61B 2018/1425; A61B 2018/1467; A61B 2018/1475; A61B 2018/00607; A61B 2018/0063; A61B 2018/00083

USPC .................. 606/41, 50–52, 205, 207, 209
See application file for complete search history.

(56) References Cited

U.S. PATENT DOCUMENTS

| 4,005,714 A | 2/1977 | Hiltebrandt |
| D249,549 S | 9/1978 | Pike |
| D263,020 S | 2/1982 | Rau, III |
| D295,893 S | 5/1988 | Sharkany et al. |

(Continued)

FOREIGN PATENT DOCUMENTS

| AU | 2011253698 A1 | 12/2011 |
| CN | 21299462 | 9/2009 |

(Continued)

OTHER PUBLICATIONS

U.S. Appl. No. 08/926,869, James G. Chandler.

(Continued)

*Primary Examiner* — Thomas Giuliani (57) ABSTRACT

A surgical instrument includes a housing, an inner shaft coupled to and extending distally from the housing, an end effector assembly disposed at a distal end of the inner shaft, an outer sheath that is fixed to the housing, extends distally from the housing, and is disposed about the inner shaft, and an insulative sleeve. The insulative sleeve is positioned between the inner shaft and the outer sheath. The insulative sleeve is movable relative to the inner shaft and the outer sheath between a storage position, wherein the insulative sleeve is positioned proximally of the end effector assembly, and a deployed position, wherein the insulative sleeve substantially surrounds the end effector assembly.

12 Claims, 7 Drawing Sheets

(56) References Cited

U.S. PATENT DOCUMENTS

| | | | |
|---|---|---|---|
| D295,894 S | 5/1988 | Sharkany et al. | |
| D298,353 S | 11/1988 | Manno | |
| D299,413 S | 1/1989 | DeCarolis | |
| 5,026,379 A | 6/1991 | Yoon | |
| D343,453 S | 1/1994 | Noda | |
| 5,312,391 A | 5/1994 | Wilk | |
| 5,318,589 A | 6/1994 | Lichtman | |
| 5,324,254 A | 6/1994 | Phillips | |
| D348,930 S | 7/1994 | Olson | |
| D349,341 S | 8/1994 | Lichtman et al. | |
| 5,342,359 A | 8/1994 | Rydell | |
| 5,368,600 A | 11/1994 | Failla et al. | |
| D354,564 S | 1/1995 | Medema | |
| 5,401,274 A | 3/1995 | Kusunoki | |
| D358,887 S | 5/1995 | Feinberg | |
| 5,411,519 A | 5/1995 | Tovey et al. | |
| 5,445,638 A | 8/1995 | Rydell et al. | |
| 5,458,598 A | 10/1995 | Feinberg et al. | |
| 5,527,313 A | 6/1996 | Scott et al. | |
| 5,556,397 A | 9/1996 | Long et al. | |
| 5,611,813 A | 3/1997 | Lichtman | |
| D384,413 S | 9/1997 | Zlock et al. | |
| 5,735,873 A | 4/1998 | MacLean | |
| 5,762,626 A | 6/1998 | Lundquist et al. | |
| H1745 H | 8/1998 | Paraschac | |
| 5,792,164 A | 8/1998 | Lakatos et al. | |
| 5,807,393 A | 9/1998 | Williamson, IV et al. | |
| D402,028 S | 12/1998 | Grimm et al. | |
| D408,018 S | 4/1999 | McNaughton | |
| 5,893,863 A | 4/1999 | Yoon | |
| 5,919,202 A | 7/1999 | Yoon | |
| D416,089 S | 11/1999 | Barton et al. | |
| 6,004,319 A | 12/1999 | Goble et al. | |
| D424,694 S | 5/2000 | Tetzlaff et al. | |
| D425,201 S | 5/2000 | Tetzlaff et al. | |
| 6,113,596 A | 9/2000 | Hooven et al. | |
| H1904 H | 10/2000 | Yates et al. | |
| 6,156,009 A | 12/2000 | Grabek | |
| 6,190,386 B1 | 2/2001 | Rydell | |
| 6,270,497 B1 | 8/2001 | Sekino et al. | |
| D449,886 S | 10/2001 | Tetzlaff et al. | |
| 6,299,625 B1 | 10/2001 | Bacher | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,387,094 B1 | 5/2002 | Eitenmuller | |
| H2037 H | 7/2002 | Yates et al. | |
| D465,281 S | 11/2002 | Lang | |
| D466,209 S | 11/2002 | Bon | |
| 6,551,313 B1 | 4/2003 | Levin | |
| 6,558,385 B1 | 5/2003 | McClurken et al. | |
| 6,679,882 B1 | 1/2004 | Kornerup | |
| D493,888 S | 8/2004 | Reschke | |
| D496,997 S | 10/2004 | Dycus et al. | |
| 6,808,525 B2 | 10/2004 | Latterell et al. | |
| D499,181 S | 11/2004 | Dycus et al. | |
| 6,837,888 B2 | 1/2005 | Ciarrocca et al. | |
| D502,994 S | 3/2005 | Blake, III | |
| D509,297 S | 9/2005 | Wells | |
| 6,942,662 B2 | 9/2005 | Goble et al. | |
| 7,033,356 B2 | 4/2006 | Latterell et al. | |
| 7,063,699 B2 | 6/2006 | Hess et al. | |
| D525,361 S | 7/2006 | Hushka | |
| D531,311 S | 10/2006 | Guerra et al. | |
| 7,128,254 B2 | 10/2006 | Shelton, IV et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| 7,208,005 B2 | 4/2007 | Frecker et al. | |
| D541,611 S | 5/2007 | Aglassinger | |
| D541,938 S | 5/2007 | Kerr et al. | |
| D545,432 S | 6/2007 | Watanabe | |
| 7,232,440 B2 * | 6/2007 | Dumbauld | A61B 18/1445 606/45 |
| D547,154 S | 7/2007 | Lee | |
| D564,662 S | 3/2008 | Moses et al. | |
| D567,943 S | 4/2008 | Moses et al. | |
| 7,367,976 B2 | 5/2008 | Lawes et al. | |
| 7,402,162 B2 | 7/2008 | Ouchi | |
| D575,395 S | 8/2008 | Hushka | |
| D575,401 S | 8/2008 | Hixson et al. | |
| 7,442,194 B2 | 10/2008 | Dumbauld et al. | |
| 7,445,621 B2 | 11/2008 | Dumbauld et al. | |
| D582,038 S | 12/2008 | Swoyer et al. | |
| 7,481,810 B2 | 1/2009 | Dumbauld et al. | |
| 7,510,562 B2 | 3/2009 | Lindsay | |
| 7,588,570 B2 | 9/2009 | Wakikaido et al. | |
| 7,658,311 B2 | 2/2010 | Boudreaux | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,758,577 B2 | 7/2010 | Nobis et al. | |
| D621,503 S | 8/2010 | Otten et al. | |
| 7,789,878 B2 | 9/2010 | Dumbauld et al. | |
| 7,815,636 B2 | 10/2010 | Ortiz | |
| 7,819,872 B2 * | 10/2010 | Johnson | A61B 17/29 606/51 |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,879,035 B2 | 2/2011 | Garrison et al. | |
| D649,249 S | 11/2011 | Guerra | |
| D649,643 S | 11/2011 | Allen, IV et al. | |
| D661,394 S | 6/2012 | Romero et al. | |
| 8,257,352 B2 | 9/2012 | Lawes et al. | |
| 8,333,765 B2 | 12/2012 | Johnson et al. | |
| 8,353,437 B2 | 1/2013 | Boudreaux | |
| 8,454,602 B2 | 6/2013 | Kerr et al. | |
| 8,523,898 B2 | 9/2013 | Bucciaglia et al. | |
| 8,529,566 B2 | 9/2013 | Kappus et al. | |
| 8,568,408 B2 | 10/2013 | Townsend et al. | |
| 8,591,510 B2 | 11/2013 | Allen, IV et al. | |
| 8,628,557 B2 | 1/2014 | Collings et al. | |
| 8,679,098 B2 | 3/2014 | Hart | |
| 8,679,140 B2 | 3/2014 | Butcher | |
| RE44,834 E | 4/2014 | Dumbauld et al. | |
| 8,685,009 B2 | 4/2014 | Chernov et al. | |
| 8,685,056 B2 | 4/2014 | Evans et al. | |
| 8,696,667 B2 | 4/2014 | Guerra et al. | |
| 8,702,737 B2 | 4/2014 | Chojin et al. | |
| 8,702,749 B2 | 4/2014 | Twomey | |
| 8,745,840 B2 | 6/2014 | Hempstead et al. | |
| 8,747,413 B2 | 6/2014 | Dycus | |
| 8,747,434 B2 | 6/2014 | Larson et al. | |
| 8,752,264 B2 | 6/2014 | Ackley et al. | |
| 8,756,785 B2 | 6/2014 | Allen, IV et al. | |
| 8,845,636 B2 | 9/2014 | Allen, IV et al. | |
| 8,852,185 B2 | 10/2014 | Twomey | |
| 8,864,753 B2 | 10/2014 | Nau, Jr. et al. | |
| 8,864,795 B2 | 10/2014 | Kerr et al. | |
| 8,887,373 B2 | 11/2014 | Brandt et al. | |
| 8,888,771 B2 | 11/2014 | Twomey | |
| 8,900,232 B2 | 12/2014 | Ourada | |
| 8,920,461 B2 | 12/2014 | Unger et al. | |
| 8,939,972 B2 | 1/2015 | Twomey | |
| 8,961,513 B2 | 2/2015 | Allen, IV et al. | |
| 8,961,514 B2 | 2/2015 | Garrison | |
| 8,961,515 B2 | 2/2015 | Twomey et al. | |
| 8,968,283 B2 | 3/2015 | Kharin | |
| 8,968,298 B2 | 3/2015 | Twomey | |
| 8,968,305 B2 | 3/2015 | Dumbauld et al. | |
| 8,968,306 B2 | 3/2015 | Unger | |
| 8,968,307 B2 | 3/2015 | Evans et al. | |
| 8,968,308 B2 | 3/2015 | Horner et al. | |
| 8,968,309 B2 | 3/2015 | Roy et al. | |
| 8,968,310 B2 | 3/2015 | Twomey et al. | |
| 8,968,311 B2 | 3/2015 | Allen, IV et al. | |
| 8,968,317 B2 | 3/2015 | Evans et al. | |

(56) References Cited

U.S. PATENT DOCUMENTS

| | | |
|---|---|---|
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,060,780 B2 | 6/2015 | Twomey et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 9,713,492 B2 * | 7/2017 | Garrison ............ A61B 18/1445 |
| 2002/0049442 A1 | 4/2002 | Roberts et al. |
| 2004/0236326 A1 | 11/2004 | Schulze et al. |
| 2005/0187547 A1 | 8/2005 | Sugi |
| 2006/0129146 A1 | 6/2006 | Dycus et al. |
| 2007/0078458 A1 | 4/2007 | Dumbauld et al. |
| 2007/0106295 A1 | 5/2007 | Garrison et al. |
| 2007/0213707 A1 | 9/2007 | Dumbauld et al. |
| 2007/0278277 A1 | 12/2007 | Wixey et al. |
| 2008/0083813 A1 | 4/2008 | Zemlok et al. |
| 2008/0215050 A1 | 9/2008 | Bakos |
| 2008/0243120 A1 | 10/2008 | Lawes et al. |
| 2009/0012556 A1 | 1/2009 | Boudreaux et al. |
| 2009/0112206 A1 | 4/2009 | Dumbauld et al. |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0171350 A1 | 7/2009 | Dycus et al. |
| 2009/0182327 A1 | 7/2009 | Unger |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0071525 A1 | 3/2011 | Dumbauld et al. |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2011/0276049 A1 | 11/2011 | Gerhardt |
| 2011/0319886 A1 | 12/2011 | Chojin et al. |
| 2012/0083827 A1 | 4/2012 | Artale et al. |
| 2012/0209263 A1 | 8/2012 | Sharp et al. |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296323 A1 | 11/2012 | Chernov et al. |
| 2012/0296371 A1 | 11/2012 | Kappus et al. |
| 2012/0303026 A1 | 11/2012 | Dycus et al. |
| 2012/0323238 A1 | 12/2012 | Tyrrell et al. |
| 2012/0330308 A1 | 12/2012 | Joseph |
| 2012/0330351 A1 | 12/2012 | Friedman et al. |
| 2013/0018364 A1 | 1/2013 | Chernov et al. |
| 2013/0022495 A1 | 1/2013 | Allen, IV et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0144284 A1 | 6/2013 | Behnke, II et al. |
| 2013/0165907 A1 | 6/2013 | Attar et al. |
| 2013/0197503 A1 | 8/2013 | Orszulak |
| 2013/0218198 A1 | 8/2013 | Larson et al. |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |
| 2014/0135758 A1 * | 5/2014 | Mueller ............ A61B 18/1445 606/41 |
| 2014/0135763 A1 * | 5/2014 | Kappus ............ A61B 18/1445 606/52 |
| 2014/0276797 A1 | 9/2014 | Batchelor et al. |
| 2015/0066027 A1 * | 3/2015 | Garrison ............ A61B 18/1445 606/51 |
| 2015/0082928 A1 * | 3/2015 | Kappus .................. F16H 21/44 74/103 |
| 2017/0151013 A1 * | 6/2017 | Kappus ............ A61B 18/1445 |
| 2017/0189099 A1 * | 7/2017 | Garrison ............ A61B 18/1445 |

FOREIGN PATENT DOCUMENTS

| | | |
|---|---|---|
| CN | 201299462 | 9/2009 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |

(56) References Cited

FOREIGN PATENT DOCUMENTS

| | | |
|---|---|---|
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 | 5/2005 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2010-035695 A | 2/2010 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 02/45589 A2 | 6/2002 |
| WO | 2005/110264 A2 | 11/2005 |
| WO | 2006021269 A1 | 3/2006 |
| WO | 05110264 A3 | 4/2006 |
| WO | 2007118608 A1 | 10/2007 |
| WO | 08/040483 A1 | 4/2008 |
| WO | 2011/018154 A1 | 2/2011 |

OTHER PUBLICATIONS

U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremeich.
Michael Choti, "Abdominoperineal Resection with the LigaSure Vessel Sealing System and LigaSure Atlas 20 cm Open Instrument"; Innovations That Work, Jun. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
E. David Crawford "Evaluation of a New Vessel Sealing Device in Urologic Cancer Surgery", 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. TT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room", 2001.

(56) References Cited

OTHER PUBLICATIONS

Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex", 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
European Search Report issued in corresponding application No. 15178543.3 dated Feb. 17, 2016.

\* cited by examiner

MULTI-FUNCTION SURGICAL INSTRUMENTS

CROSS REFERENCE TO RELATED APPLICATION

The present application claims the benefit of and priority to U.S. Provisional Application Ser. No. 62/051,407, filed on Sep. 17, 2014, the entire contents of which are incorporated herein by reference.

BACKGROUND

Technical Field

The present disclosure relates to surgical instruments and, more particularly, to multi-function surgical instruments capable of treating tissue in both a bipolar mode of operation and a monopolar mode of operation.

Background of Related Art

Bipolar surgical instruments typically include two generally opposing electrodes charged to different electric potentials to selectively apply energy to tissue. Bipolar electrosurgical forceps, for example, utilize both mechanical clamping action and electrical energy to effect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be sealed. Further, it may be beneficial, particularly with respect to endoscopic surgical procedures, to provide a single instrument incorporating both bipolar and monopolar features, thereby obviating the need to alternatingly remove and insert the bipolar and monopolar instruments in favor of one another.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a surgical instrument is provided including a housing, and inner shaft, an end effector assembly, an outer sheath, and an insulative sleeve. The inner shaft is coupled to and extends distally from the housing. The end effector assembly is disposed at a distal end of the inner shaft. The outer sheath is fixed to the housing, extends distally from the housing, and is disposed about the inner shaft. The insulative sleeve is positioned between the inner shaft and the outer sheath and is movable relative to the inner shaft and the outer sheath between a storage position and a deployed position. In the storage position, the insulative sleeve is positioned proximally of the end effector assembly. In the deployed position, the insulative sleeve substantially surrounds the end effector assembly.

In an aspect of the present disclosure, the insulative sleeve and the inner shaft are rotatable in conjunction with one another and relative to the outer sheath and the housing.

In another aspect of the present disclosure, the insulative sleeve includes a proximal portion and a distal portion. The distal portion defines a diameter larger than that of the proximal portion to facilitate deployment of the insulative sleeve about the end effector assembly.

In another aspect of the present disclosure, an energizable member is coupled to the insulative sleeve and movable in conjunction with the insulative sleeve between the storage position and the deployed position. In the deployed position, the energizable member extends distally from the insulative sleeve and the end effector assembly.

In yet another aspect of the present disclosure, the end effector assembly includes first and second jaw members configured to supply bipolar energy to tissue, while the energizable member is configured to supply monopolar energy to tissue.

In still another aspect of the present disclosure, the energizable member is positioned between the inner shaft and the outer sheath.

In still yet another aspect of the present disclosure, a portion of the inner shaft extends distally from the outer sheath such that the end effector assembly is spaced-apart from the outer sheath.

Provided in accordance with other aspects of the present disclosure is a surgical instrument including a shaft assembly having an end effector assembly disposed at a distal end thereof, and an insulative sleeve segment coupled to the shaft assembly. The shaft assembly includes an insulative tube having a proximal portion and a distal portion. The insulative sleeve segment is disposed about the distal portion of the insulative tube and is movable relative to the insulative tube between a storage position and a deployed position. In the storage position, the insulative sleeve segment is positioned adjacent the proximal portion of the insulative tube and proximally of the end effector assembly. In the deployed position, the insulative sleeve segment is spaced-apart from the proximal portion of the insulative tube and substantially surrounds the end effector assembly.

In an aspect of the present disclosure, the shaft assembly includes an outer shaft having the end effector disposed at a distal end thereof. In such aspects, the outer shaft is disposed within and coupled to the insulative tube.

In another aspect of the present disclosure, the proximal portion of the insulative tube partially overlaps the distal portion of the insulative tube to define a raised annular shoulder therebetween. In such aspects, the insulative sleeve segment and raised annular shoulder may define similar diameters such that, in the storage position, the insulative sleeve segment is positioned adjacent the raised annular shoulder so as to form a continuous tubular body.

In yet another aspect of the present disclosure, an energizable member is coupled to the insulative sleeve segment and movable in conjunction with the insulative sleeve between the storage position and the deployed position. In the deployed position, the energizable member extends distally from the insulative sleeve segment and the end effector assembly.

In still another aspect of the present disclosure, the energizable member is fixed relative to the insulative sleeve segment via a bonding ring and/or an insulative ferrule.

In still yet another aspect of the present disclosure, the energizable member extends proximally through the shaft assembly. A proximal end of the energizable member is coupled to a deployment mechanism for selectively deploying the energizable member and the insulative sleeve segment.

In another aspect of the present disclosure, the end effector assembly includes first and second jaw members configured to supply bipolar energy to tissue, while the energizable member is configured to supply monopolar energy to tissue.

Another surgical instrument provided in accordance with aspects of the present disclosure includes an end effector assembly having a pair of jaw members. Each jaw member includes a distal jaw body and a proximal jaw flange. The distal jaw body of each jaw member defines an opposed surface. The proximal flanges of the jaw members are pivotably coupled to one another for moving one or both of the jaw members relative to the other between a spaced-apart position and an approximated position to grasp tissue between the opposed surfaces. A spatula-shaped energizable member is operably coupled to the end effector assembly. The spatula-shaped energizable member is movable between a storage position, wherein a distal end of the spatula-shaped energizable member is positioned towards proximal ends of the jaw bodies of the jaw members distally of the proximal flanges of the jaw members, and a deployed position, wherein the distal end of the spatula-shaped energizable member extends distally from the jaw bodies of the jaw members.

In an aspect of the present disclosure, the spatula-shaped energizable member is offset relative to the end effector assembly so as to extend adjacent an exterior surface of one of the jaw members. In such aspects, the spatula-shaped energizable member may further be configured so as to not extend beyond the opposed surface of the one jaw member towards the other jaw member.

In another aspect of the present disclosure, an insulative sleeve is disposed about the spatula-shaped energizable member and movable in conjunction with the spatula-shaped energizable member between the storage position and the deployed condition. In the storage condition, the insulative sleeve is positioned proximally of the end effector assembly. In the deployed position, the insulative sleeve substantially surrounds the end effector assembly.

In yet another aspect of the present disclosure, the jaw members are configured to supply bipolar energy to tissue, while the spatula-shaped energizable member is configured to supply monopolar energy to tissue.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
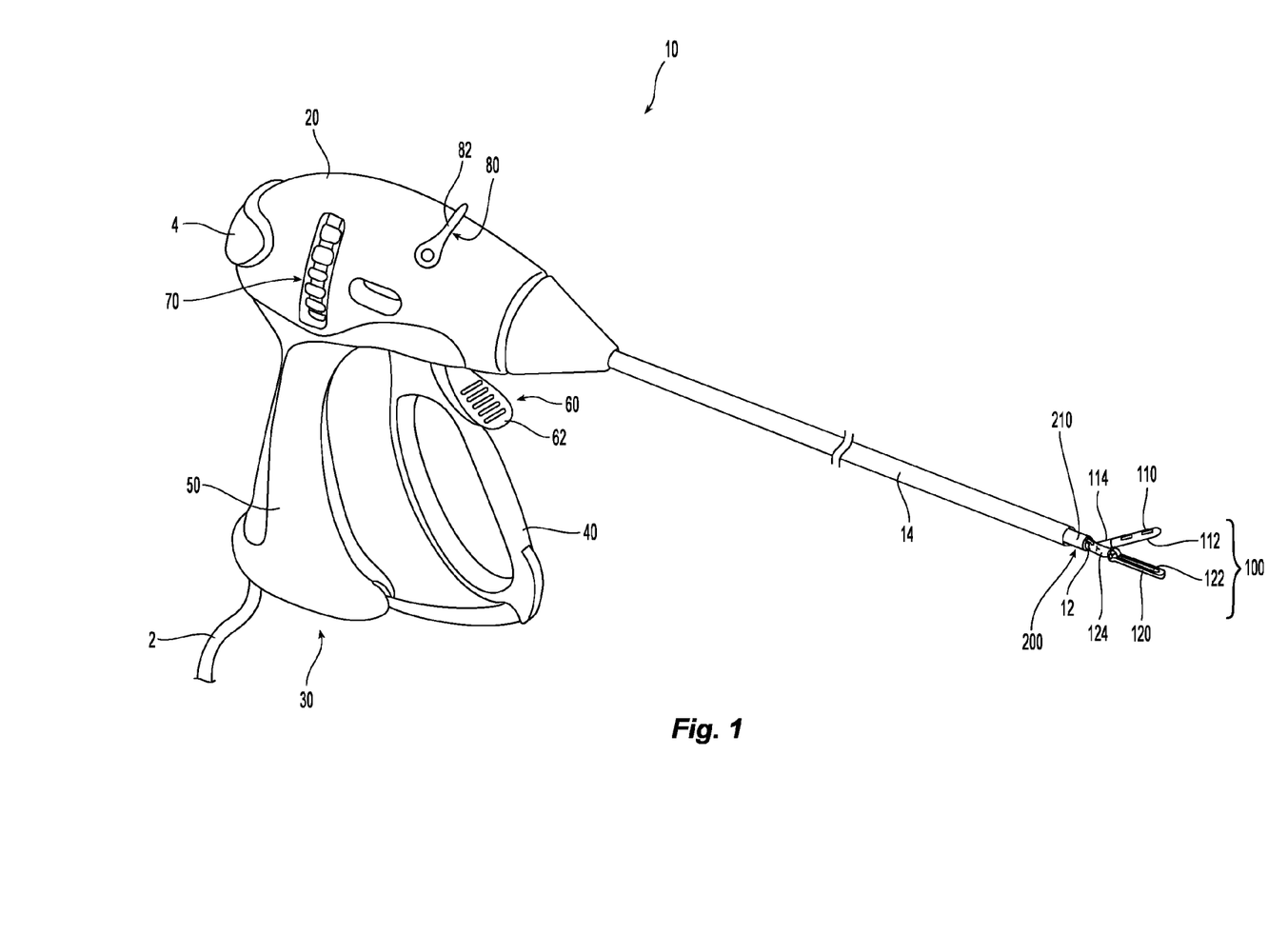
FIG. 1 is a front, perspective view of an endoscopic surgical forceps configured for use in accordance with the present disclosure.

Referring generally to FIG. 1, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Forceps 10 generally includes a housing 20, a handle assembly 30, a trigger assembly 60, a rotating assembly 70, a deployment assembly 80, an end effector assembly 100, and a monopolar assembly 200. Forceps 10 further includes an inner shaft 12 having a distal end that mechanically engages end effector assembly 100 and a proximal end that rotatably couples to housing 20, and an outer sheath 14 that is both translationally and rotationally fixed relative to housing 20. Outer sheath 14 extends distally from housing 20 to surround at least a portion of shaft 12 and monopolar assembly 200, the importance of which is detailed below.

Forceps 10 also includes an electrosurgical cable 2 that connects forceps 10 to a generator (not shown) or other suitable power source, although forceps 10 may alternatively be configured as a battery powered instrument. Cable 2 includes wires (not shown) extending therethrough that have sufficient length to extend through shaft 12 in order to provide electrical energy to at least one of the electrically-conductive surfaces 112, 122 (FIG. 2A) of jaw members 110, 120, respectively, of end effector assembly 100, e.g., upon activation of activation switch 4 in a bipolar mode. One or more of the wires (not shown) of cable 2 extends through housing 20 in order to provide electrical energy to monopolar assembly 200, e.g., upon activation of activation switch 4 in a monopolar mode. Rotating assembly 70 is rotatable in either direction to rotate end effector assembly 100 and monopolar assembly 200 relative to housing 20. Housing 20 houses the internal working components of forceps 10.

Figure 2A:
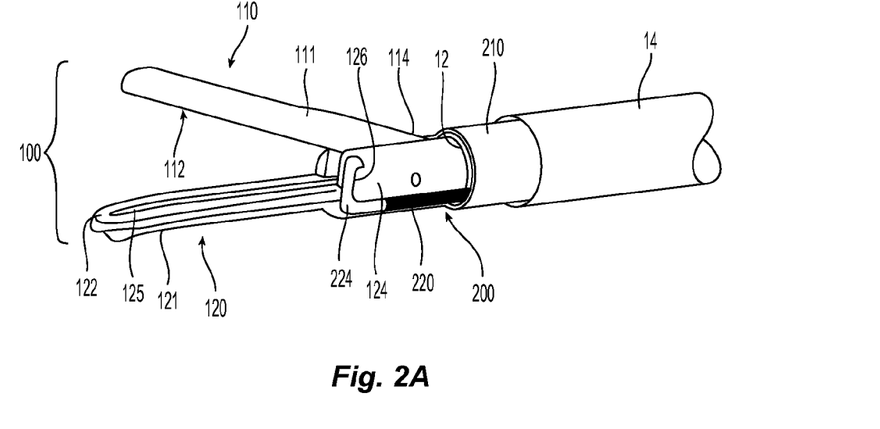
FIG. 2A is an enlarged, front, perspective view of an end effector assembly of the forceps of FIG. 1, wherein jaw members of the end effector assembly are disposed in a spaced-apart position and wherein a monopolar assembly is disposed in a storage condition.
Figure 2B:
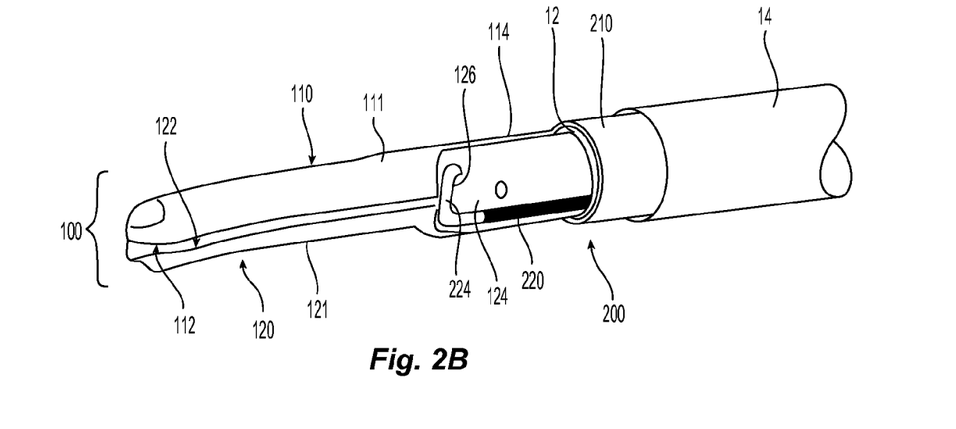
FIG. 2B is an enlarged, front, perspective view of the end effector assembly of FIG. 2A, wherein the jaw members are disposed in an approximated position and wherein the monopolar assembly is disposed in the storage condition.
Figure 2C:
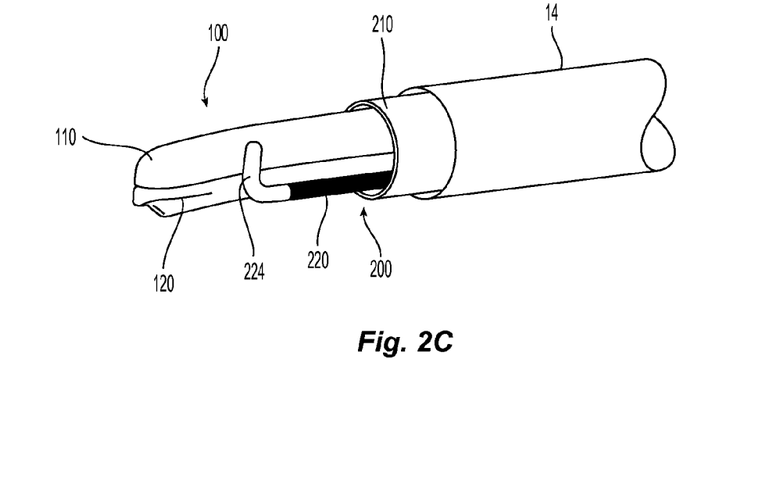
FIG. 2C is an enlarged, front, perspective view of the end effector assembly of FIG. 2A, wherein the jaw members are disposed in the approximated position and wherein the monopolar assembly is transitioning from the storage condition to a deployed condition.

Referring to FIGS. 2A-2B, end effector assembly 100 is attached at the distal end of shaft 12 and includes opposing jaw members 110, 120 pivotably coupled to one another. Each of the jaw members 110 and 120 includes a jaw body 111, 121 supporting the respective electrically-conductive surface 112, 122, and a respective proximally-extending jaw flange 114, 124. Flanges 114, 124 are pivotably coupled to one another to permit movement of jaw members 110, 120 relative to one another between a spaced-apart position (FIG. 2A) and an approximated position (FIG. 2B) for grasping tissue between surfaces 112, 122. One or both of surfaces 112, 122 are adapted to connect to a source of energy (not explicitly shown), e.g., via the wires (not shown) of cable 2 (FIG. 1) and are configured to conduct energy through tissue grasped therebetween to treat, e.g., seal, tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. Activation switch 4 (FIG. 1) is operably coupled between the source of energy (not shown) and surfaces 112, 122, thus allowing the user to selectively apply energy to surfaces 112, 122 of jaw members 110, 120, respectively, of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 125 may be defined within one or both of jaw members 110, 120 to permit reciprocation of a knife (not shown) therethrough, e.g., upon actuation of a trigger 62 of trigger assembly 60, to cut tissue grasped between jaw members 110, 120.

Figure 2D:
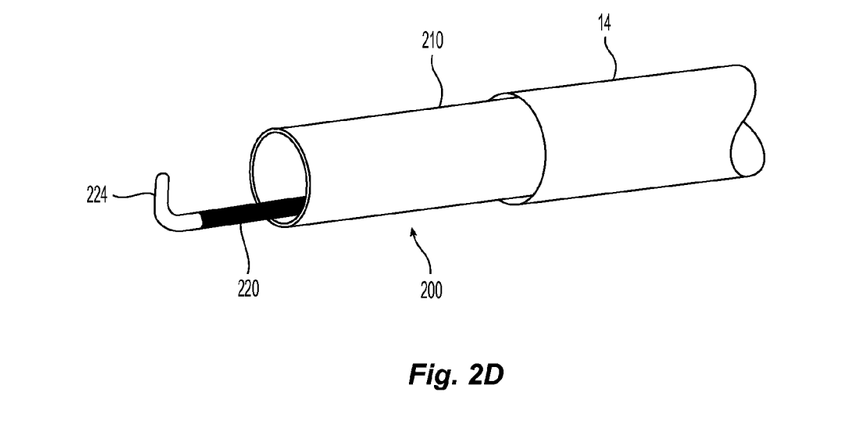
FIG. 2D is an enlarged, front, perspective view of the end effector assembly of FIG. 2A, wherein the monopolar assembly is disposed in the deployed condition.

Referring to FIGS. 1-2D, monopolar assembly 200 includes an insulative sleeve 210 and an energizable rod member 220. Insulative sleeve 210 is slidably disposed within outer sheath 14 and about inner shaft 12, e.g., inner shaft 12, insulative sleeve 210, and outer sheath 14 may be coaxially disposed about one another. As noted above, inner shaft 12 and outer sheath 14 are translationally fixed relative to one another, although inner shaft 12 is rotatable relative to outer sheath 14 and housing 20 to permit rotation of end effector assembly 100 relative to housing 20, e.g., upon actuation of rotating assembly 70. Insulative sleeve 210 is selectively movable relative to inner shaft 12, outer sleeve 14, and end effector assembly 100 between a storage position (FIGS. 2A and 2B), wherein insulative sleeve 210 is disposed proximally of end effector assembly 100, and a deployed position (FIG. 2D), wherein insulative sleeve 210 is substantially disposed about end effector assembly 100 so as to electrically insulate surfaces 112, 122 of jaw members 110, 120, respectively.

Energizable rod member 220 of monopolar assembly 200 extends from housing 20, through outer sheath 14, insulative sleeve 210, and, optionally, inner shaft 12. Energizable rod member 220 extends distally from outer sheath 14, insulative sleeve 210, and, inner shaft 12, ultimately defining an electrically-conductive distal tip 224. Energizable rod member 220 and, more specifically, distal tip 224 thereof, functions as the active electrode of monopolar assembly 200. The one or more wires (not shown) extending from cable 2 through housing 20 (see FIG. 1), are coupled to energizable rod member 220 within housing 20 to provide energy to energizable rod member 220, e.g., upon actuation of activation switch 4 (FIG. 1) in a monopolar mode, for treating tissue in a monopolar mode of operation. Energizable rod member 220 is movable between a storage position (FIG. 2B) and a deployed position (FIG. 2D). In the storage position (FIG. 2B), distal tip 224 of rod member 220 is disposed within an insulated groove 126 defined within proximal flange 124 of jaw member 120, although other configurations are also contemplated. Insulated groove 126 electrically-insulates distal tip 224 of rod member 220 from electrically-conductive surfaces 112, 122 of jaw members 110, 120, respectively, and from surrounding tissue when disposed in the storage position. Alternatively, distal tip 224 of rod member 220 may only be insulated from surface 112. In such configurations, distal tip 224 of rod member 220 is capable of being energized to the same polarity as surface 122. Distal tip 224 may be hook-shaped (as shown), or may define any other suitable configuration, e.g., linear, ball, circular, angled, etc.

Both insulative sleeve 210 and rod member 220 of monopolar assembly 200 are coupled to deployment assembly 80, such that insulative sleeve 210 and rod member 220 move in concert with one another between their storage positions (FIGS. 2A and 2B), collectively the storage condition of monopolar assembly 200, and their deployed positions (FIG. 2D), collectively the deployed condition of monopolar assembly 200. Deployment assembly 80 includes a rotatable deployment lever 82 pivotably mounted on housing 20, and may further include any suitable pivots, gears, linkages, etc., disposed within housing 20 for selectively translating insulative sleeve 210 and rod member 220 relative to housing 20 in response to rotation of deployment lever 82 relative to housing 20. Thus, deployment lever 82 is movable between an un-actuated position, corresponding to the storage condition of monopolar assembly 200 (FIGS. 2A and 2B), and an actuated position, corresponding to the deployed condition of monopolar assembly 200 (FIG. 2D), for deploying monopolar assembly 200. In the deployed condition, as shown in FIG. 2D, distal tip 224 of rod member 220 of monopolar assembly 200 extends distally from end effector assembly 100 and insulative sleeve 210, which substantially surrounds end effector assembly 100. In this position, energy may be applied to distal tip 224 of rod member 220 to treat tissue, e.g., via activation of activation switch 4 (FIG. 1) in the monopolar mode.

With reference again to FIG. 1, handle assembly 30 includes a movable handle 40 and a fixed handle 50. Fixed handle 50 is integrally associated with housing 20 and movable handle 40 is movable relative to fixed handle 50.

Movable handle 40 is movable relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position. Movable handle 40 is ultimately connected to a drive assembly (not shown) disposed within housing 20 that, together, mechanically cooperate to impart movement of jaw members 110, 120 between the spaced-apart position (FIG. 2A), corresponding to the initial position of movable handle 40, and the approximated position (FIG. 2B), corresponding to the compressed position of movable handle 40. Any suitable drive assembly for this purpose may be provided.

Trigger assembly 60 includes trigger 62 that is operably coupled to a knife (not shown). Trigger 62 of trigger assembly 60 is selectively actuatable to advance the knife from a retracted position, wherein the knife is disposed proximally of jaw members 110, 120, to an extended position, wherein the knife extends at least partially between jaw members 110, 120 and through knife channel(s) 125 (FIG. 2A) to cut tissue grasped between jaw members 110, 120.

Referring to FIGS. 1-2D, the use and operation of forceps 10 in both the bipolar mode, e.g., for grasping, treating and/or cutting tissue, and the monopolar mode, e.g., for electrical/electromechanical tissue treatment, is described. Turning to FIGS. 1 and 2A, with respect to the bipolar mode, initially, deployment lever 82 is moved to (or remains in) the un-actuated position, corresponding to the storage condition of monopolar assembly 200, wherein insulative sleeve 210 is positioned proximally of jaw members 110, 120, and distal tip 224 of energizable rod member 220 is disposed within insulative groove 126 of jaw flange 124 of jaw member 120. At this point, movable handle 40 is disposed in its initial position such that jaw members 110, 120 are disposed in the spaced-apart position. Further, trigger 62 of trigger assembly 60 remains un-actuated such that the knife remains disposed in its retracted position.

Continuing with reference to FIGS. 1 and 2A, with jaw members 110, 120 disposed in the spaced-apart position (FIG. 2A), end effector assembly 100 may be maneuvered into position such that tissue to be grasped, treated, e.g., sealed, and/or cut, is disposed between jaw members 110, 120. Additionally or alternatively, rotating assembly 70 may be actuated to selectively rotate end effector assembly 100 relative to housing 20 and outer sheath 14 to better position end effector assembly 100 relative to tissue. Once end effector assembly 100 is positioned as desired, movable handle 40 is depressed, or pulled proximally relative to fixed handle 50 such that jaw member 110 is pivoted relative to jaw member 120 from the spaced-apart position to the approximated position to grasp tissue therebetween, as shown in FIG. 2B. In this approximated position, energy may be supplied, e.g., via activation of switch 4, to surface 112 of jaw member 110 and/or surface 122 of jaw member 120 and conducted through tissue to treat tissue, e.g., to effect a tissue seal or otherwise treat tissue in the bipolar mode of operation. Once tissue treatment is complete (or to cut untreated tissue), the knife may be deployed from within shaft 12 to between jaw members 110, 120, e.g., via actuation of trigger 62 of trigger assembly 60, to cut tissue grasped between jaw members 110, 120.

When tissue cutting is complete, trigger 62 may be released to return the knife to the retracted position. Thereafter, movable handle 40 may be released or returned to its initial position such that jaw members 110, 120 are moved back to the spaced-apart position (FIG. 2A) to release the treated and/or divided tissue.

For operation of forceps 10 in the monopolar mode, jaw members 110, 120 are first moved to the approximated position, e.g., by depressing movable handle 40 relative to fixed handle 50. Once the approximated position has been achieved, monopolar assembly 200 may be deployed. In order to deploy monopolar assembly 200, deployment lever 82 of deployment assembly 80 is rotated from the un-actuated position to the actuated position. As such, insulative sleeve 210 and energizable rod member 220 are advanced distally relative to inner shaft 12, outer sheath 14, and end effector assembly 100 from the position shown in FIG. 2B, through the position shown in FIG. 2C, to the position shown in FIG. 2D.

With monopolar assembly 200 disposed in the deployed condition, forceps 10 may be manipulated and/or rotating assembly 70 actuated to position energizable rod member 220 as desired. Once energizable rod member 220 is positioned as desired, activation switch 4 may be actuated to supply energy to energizable rod member 220 to treat, e.g., dissect or otherwise treat, tissue. During application of energy to tissue via energizable rod member 220, forceps 10 may be moved relative to tissue, e.g., longitudinally, transversely, and/or radially, to facilitate electromechanical treatment of tissue. At the completion of tissue treatment, monopolar assembly 200 may be returned to the storage condition, e.g., by returning deployment lever 82 to the un-actuated position.

As noted above, outer sheath 14 is fixed relative to housing 20 and is disposed about insulative sleeve 210 and shaft 12. As such, tissue and/or other devices or equipment are inhibited from contacting insulative sleeve 210 or shaft 12 substantially along the lengths thereof, except for the exposed distal portions of insulative sleeve 210 and shaft 12. As a result of this protection provided by fixed outer sheath 14, insulative sleeve 210 is permitted to be advanced and retracted during use without substantially contacting, interfering with, or creating friction against tissue and/or other devices or equipment. Likewise, the protection provided by fixed outer sheath 14 permits shaft 12 and insulative sleeve 210 to be rotated during use without contacting, interfering with, or creating friction against tissue and/or other devices or equipment. The above-noted feature is particularly advantageous for use in endoscopic surgical procedures although the benefits of such a feature can also be readily appreciated in various other types of procedures. With respect to endoscopic surgical procedures, an access device is positioned within an opening in tissue to provide access to the internal surgical site.

Forceps 10 is then inserted through such an access device and, once positioned therein, outer sheath 14 remains relatively stationary relative to the access device during rotation of end effector assembly 100 and monopolar assembly 200, and deployment/retraction of monopolar assembly 200, thus inhibiting catching or interfering with the access device or other instruments inserted therethrough. In addition, with respect to endoscopic procedures performed under insufflation, the access device typically includes one or more seals deigned to establish a fluid-tight seal about instrumentation inserted therethrough, thereby helping to maintain the internal surgical site in an insufflated state. With respect to forceps 10 being inserted through such an access device, the fluid-tight seal would be formed about outer sheath 14, which remains relatively stationary relative to the access device during rotation of end effector assembly 100 and monopolar assembly 200, and deployment/retraction of monopolar assembly 200, thus helping to maintain an effective seal about outer sheath 14.

Turning now to FIGS. 3A-4B, another forceps 310 provided in accordance with the present disclosure, similar to forceps 10 (FIG. 1), is shown. Forceps 310 includes a shaft assembly 312, an end effector assembly 400 disposed at a distal end of shaft assembly 312, and a monopolar assembly 500 coupled to shaft assembly 312 towards the distal end thereof. Although only the distal portion of forceps 310 is shown, forceps further includes any of the aspects and features detailed above with respect to forceps 10 (FIG. 1), e.g., a housing, handle assembly, trigger assembly, rotating assembly, deployment assembly, as well as other functional components that enable operation of forceps 310, similarly as detailed above with respect to forceps 10 (FIG. 1). For purposes of brevity, forceps 310 will be detailed hereinbelow with respect to those components and/or features that differ from forceps 10 (FIG. 1) or those that were not specifically detailed above with respect to forceps 10 (FIG. 1).

Shaft assembly 312 of forceps 310 includes an outer shaft 314 and an insulative tube 316 disposed about outer shaft 314. Outer shaft 314 is coupled to the housing (not shown) of forceps 310 at its proximal end and includes end effector assembly 400 coupled thereto at its distal end. More specifically, jaw member 420 of end effector assembly 400 may be fixed relative to outer shaft 314 while jaw member 410 is movable relative to both outer shaft 314 and fixed jaw member 420, although other configurations are also contemplated. A inner shaft 340 of the drive assembly of forceps 310 is slidably disposed within outer shaft 314 and coupled to jaw member 410 and/or jaw member 420 such that reciprocation of inner shaft 340 through outer shaft 314 and relative to jaw members 410, 420, e.g., upon actuation of the movable handle of forceps 310, pivots jaw member 410, 420 between a spaced-apart position and an approximated position for grasping tissue therebetween. As detailed below, outer shaft 314 further includes an opening 315, e.g., a slot, aperture, etc., defined towards the distal end thereof to permit energizable rod member 520 of monopolar assembly 500 to extend therethrough, although energizable rod member 520 may alternatively be disposed entirely exteriorly of outer shaft 314, e.g., between outer shaft 314 and insulative tube 316.

Insulative tube 316, as mentioned above, is disposed about outer shaft 314. More specifically, insulative tube 316 may be disposed in surrounding contact with outer shaft 314. Insulative tube 316 is coupled to outer shaft 314, e.g., via adhesion, bonding, mechanical coupling, or any other suitable engagement, so as to be maintained in fixed relation relative to outer shaft 314. Insulative tube 316 includes a proximal portion 317 and a distal portion 319. Proximal portion 317 at least partially overlaps distal portion 319 (FIGS. 4A-4B) and defines a raised annular shoulder 318 adjacent the meeting of proximal and distal portions 317, 319. The overlapping segment of proximal portion 317 may be joined with the underlying segment of distal portion 319 so as to inhibit fluid ingress therebetween, although other configurations are also contemplated.

Figure 3A:
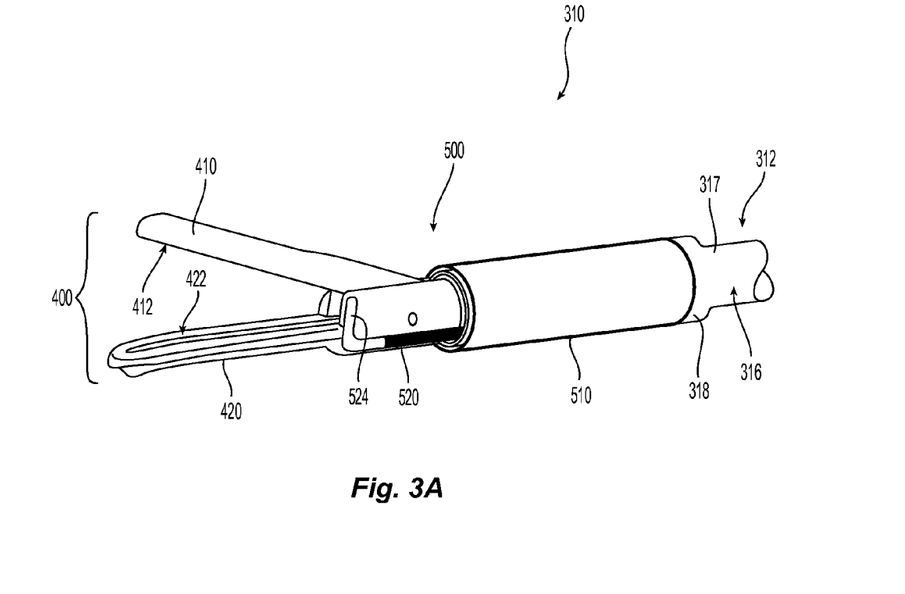
FIG. 3A is an enlarged, front, perspective view of an end effector assembly of another forceps provided in accordance with the present disclosure, similar to the forceps of FIG. 1, and wherein jaw members of the end effector assembly are disposed in a spaced-apart position and a monopolar assembly is disposed in a storage condition.
Figure 3B:
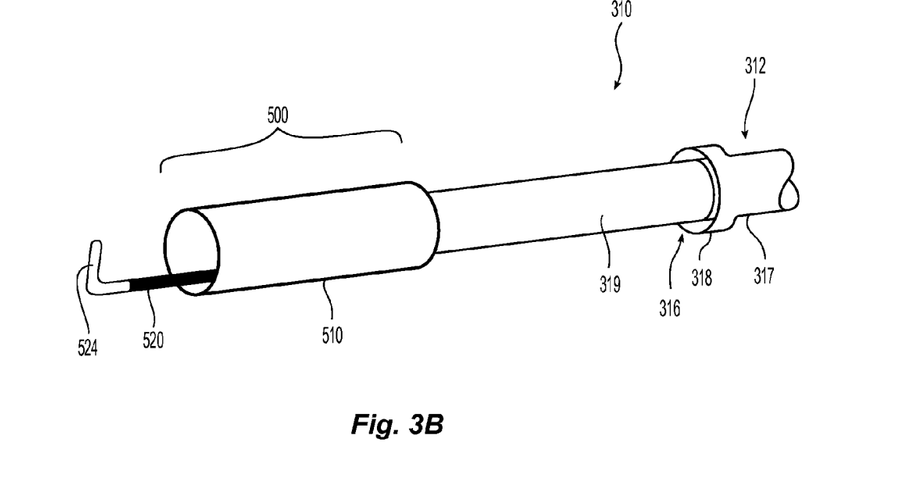
FIG. 3B is an enlarged, front, perspective view of the end effector assembly of FIG. 3A, wherein the monopolar assembly is disposed in a deployed condition.
Figure 4A:
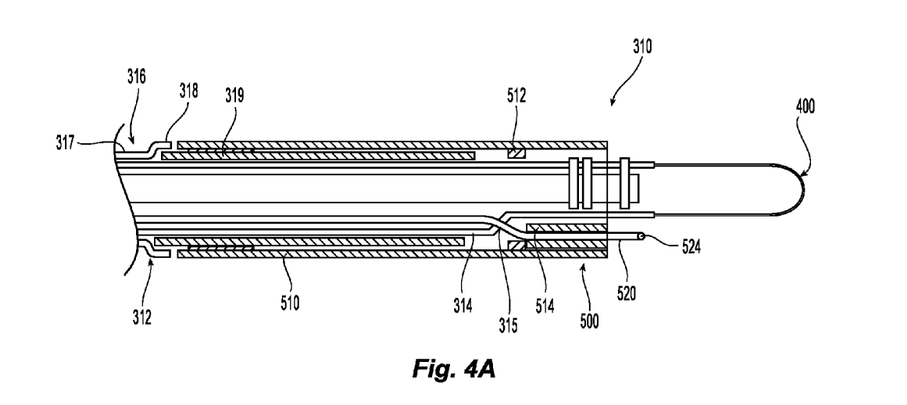
FIG. 4A is a top, longitudinal, cross-sectional view of the end effector assembly of FIG. 3A, wherein the jaw members are disposed in an approximated position and wherein the monopolar assembly is disposed in the storage condition.
Figure 4B:
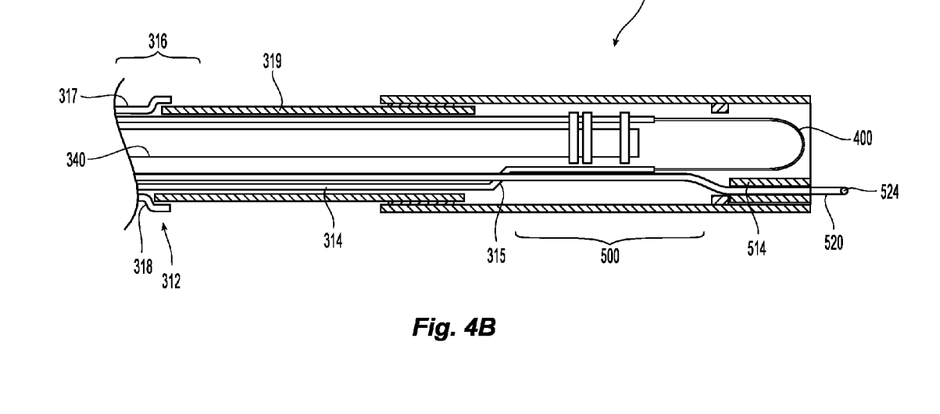
FIG. 4B is a top, longitudinal, cross-sectional view of the end effector assembly of FIG. 3A, wherein the jaw members are disposed in the approximated position and wherein the monopolar assembly is disposed in the deployed condition.

Continuing with reference to FIGS. 3A-4B, monopolar assembly 500 of forceps 310 includes an insulative sleeve segment 510 and an energizable rod member 520. Insulative sleeve segment 510 is slidably disposed about distal portion 319 of insulative tube 316 of shaft assembly 312. Insulative sleeve segment 510 is selectively movable relative to shaft assembly 312 and end effector assembly 400 between a storage position (FIGS. 3A and 4A) and a deployed position (FIGS. 3B and 4B). In the storage position, the distal end of insulative sleeve segment 510 is disposed proximally of end effector assembly 400, while the proximal end of insulative sleeve segment 510 is disposed in abutment with the raised annular shoulder 318 defined between proximal and distal portions 317, 319 of insulative tube 316. The diameter of raised annular shoulder 318 may approximate that of insulative sleeve segment 510 or may otherwise be configured so as to from a tubular body having an enlarged-diameter distal portion, e.g., the portion encompassing raised annular shoulder 318 and insulative sleeve segment 510.

In the deployed position, insulative sleeve segment 510 is spaced-apart from raised annular shoulder 318 to expose a portion of distal portion 319 of insulative tube 316 and is substantially disposed about end effector assembly 400 so as to electrically insulate surfaces 412, 422 of jaw members 410, 420, respectively. Insulative sleeve segment 510 may further include a bonding ring 512 disposed on an interior surface thereof and/or an insulative ferrule 514 disposed on an interior surface thereof for securing energizable rod member 520 and insulative sleeve segment 510 to one another.

Energizable rod member 520 of monopolar assembly 500 extends from the housing of forceps 310 through outer shaft 314 (or, alternatively, between outer shaft 314 and insulative tube 316). Energizable rod member 520 extends distally from shaft assembly 312, e.g., through opening 315 defined within outer shaft 314, ultimately defining an electrically-conductive distal tip 524 that functions as the active electrode of monopolar assembly 500. Energizable rod member 520 is movable between a storage position (FIGS. 3A and 4A) and a deployed position (FIGS. 3B and 4B), similarly as detailed above with respect to energizable rod member 220 of monopolar assembly 200 of forceps 10 (FIGS. 1-2D). In the storage position energizable rod member 520 may be positioned adjacent the proximal flange of jaw member 420 (as shown), or may be positioned within a groove defined within the proximal flange, similarly as detailed above with respect to forceps 10 (FIG. 1).

At the proximal end of energizable rod member 520, which is disposed within the housing of forceps 310, one or more wires (not shown) couple to energizable rod member 520 to provide energy thereto for treating tissue in a monopolar mode of operation. Further, the proximal end of energizable rod member 520 is coupled to the deployment assembly of forceps 310 to permit selective deployment/retraction of rod member 520 and insulative sleeve segment 510. As noted above, insulative sleeve segment 510 is coupled to rod member 520 via bonding ring 512 and/or insulative ferrule 514 and, as such, insulative sleeve segment 510 and rod member 520 move in concert with one another between their storage positions (FIGS. 3A and 4A), collectively the storage condition of monopolar assembly 500, and their deployed positions (FIGS. 3B and 4BD), collectively the deployed condition of monopolar assembly 500. The deployment assembly for forceps 310 may be similar to that of forceps 10 (FIG. 1), any may include any suitable pivots, gears, linkages, etc., for selectively translating rod member 520 and, thus, insulative sleeve segment 510 between the storage and deployed conditions. In the deployed condition, as shown in FIGS. 3B and 4B, distal tip 524 of rod member 520 of monopolar assembly 500 extends distally from end effector assembly 400 and insulative sleeve segment 510, which substantially surrounds end effector assembly 400, so as to permit distal tip 524 of rod member 520 to be utilized to dissect or otherwise treat tissue.

The use and operation of forceps 310 is similar to that of forceps 10 (FIG. 1), detailed above, and, thus, will not be detailed hereinbelow. Likewise, the above-detailed advantages of forceps 10 (FIG. 1) apply similarly to forceps 310. That is, with insulative tube 316 fixed in position and with insulative sleeve segment 510 only sliding about distal portion 319 of insulative tube 316, insulative sleeve segment 510 may be advanced and retracted during use with minimal contact, interference, or friction against tissue and/or other devices or equipment.

Figure 5:
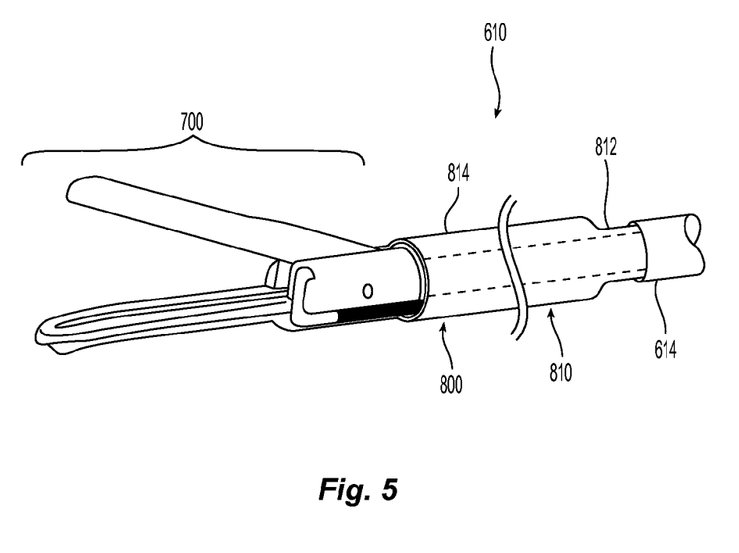
FIG. 5 is an enlarged, front, perspective view of an end effector assembly of another forceps provided in accordance with the present disclosure, similar to the forceps of FIG. 1, wherein jaw members of the end effector assembly are disposed in a spaced-apart position and a monopolar assembly is disposed in a storage condition.

Referring to FIG. 5, another forceps 610 provided in accordance with present disclosure is shown. Although only the distal end of forceps 610 is shown, forceps 610 is similar to and may include any of the features of forceps 10 (FIG. 1), detailed above. Forceps 610 differs from forceps 10 (FIG. 1) in that insulative sleeve 810 of monopolar assembly 800 of forceps 610 includes a proximal portion 812 and a distal portion 814 having a diameter greater than that of proximal portion 812. Proximal portion 812 is substantially disposed within outer sheath 614 of forceps 610. Enlarged-diameter distal portion 814 extends distally from outer sheath 614 and provides additional clearance to facilitate the deployment of insulative sleeve 810 about end effector assembly 700 of forceps 610.

Figure 6A:
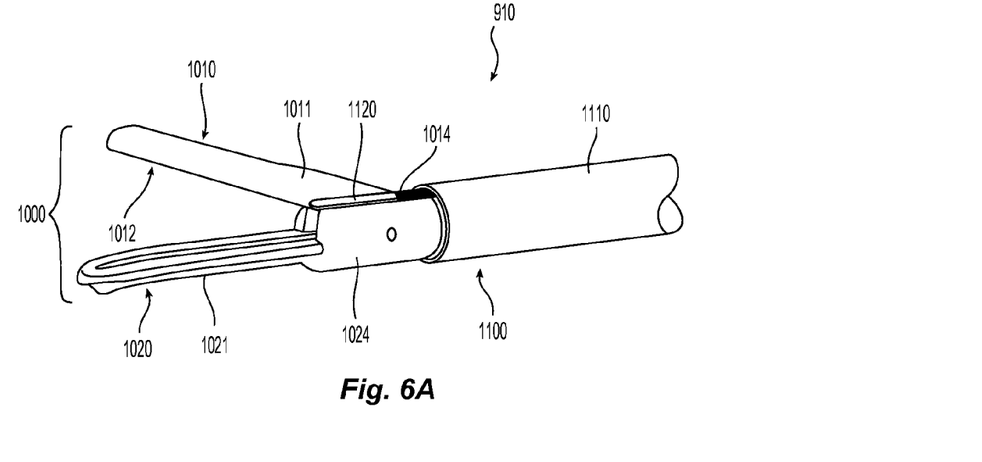
FIG. 6A is an enlarged, front, perspective view of an end effector assembly of another forceps provided in accordance with the present disclosure, similar to the forceps of FIG. 1, and wherein jaw members of the end effector assembly are disposed in a spaced-apart position and wherein a monopolar assembly is disposed in a storage condition.
Figure 6B:
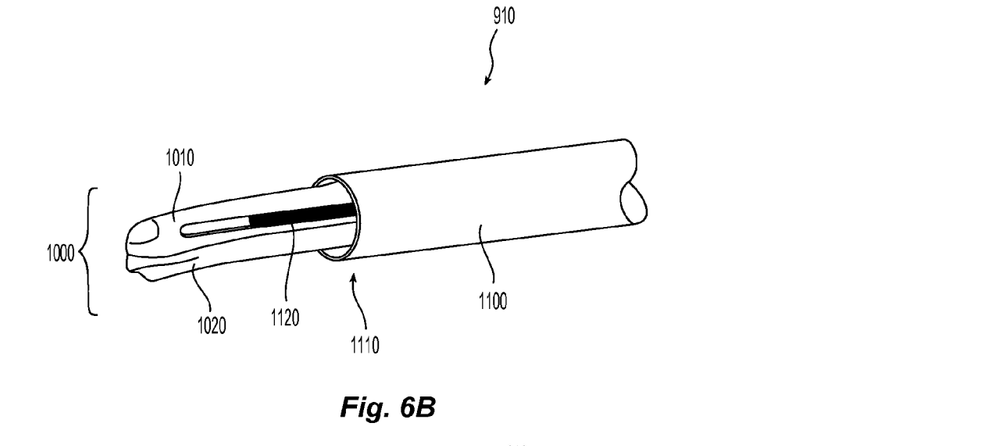
FIG. 6B is an enlarged, front, perspective view of the end effector assembly of FIG. 6A, wherein the jaw members are disposed in the approximated position and wherein the monopolar assembly is transitioning from the storage condition to a deployed condition.
Figure 6C:
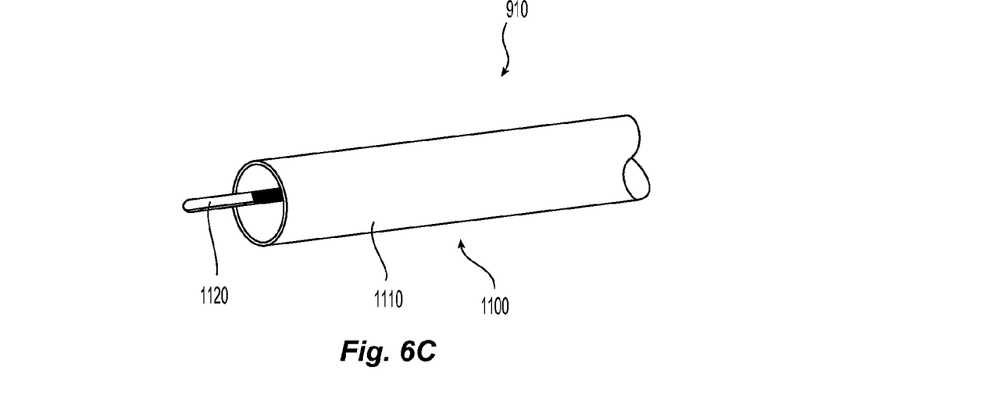
FIG. 6C is an enlarged, front, perspective view of the end effector assembly of FIG. 6A, wherein the monopolar assembly is disposed in the deployed condition.

Turning now to FIGS. 6A-6C, another forceps 910 provided in accordance with present disclosure is shown. Although only the distal end of forceps 910 is shown, forceps 910 may be configured similarly to and may include any of the features of any of the forceps detailed above, e.g., forceps 10 (FIG. 1). Forceps 910 differs from the forceps detailed above in that monopolar assembly 1100 of forceps 910 includes, in addition to an insulative sleeve 1110, a spatula-shaped energizable member 1120. Spatula-shaped energizable member 1120, similar to the energizable rod member 220 of forceps 10 (FIGS. 1 and 2A), is configured to move in conjunction with the insulative sleeve 1110 between a storage condition (FIG. 6A) and a deployed condition (FIG. 6C).

In the storage condition of monopolar assembly 1100, as shown in FIG. 6A, insulative sleeve 1110 is positioned proximally of end effector assembly 1000 and spatula-shaped energizable member 1120 is retracted so as not to extend distally from jaw members 1010, 1020. However, spatula-shaped energizable member 1120 is not fully retracted as with energizable rod member 220 of monopolar assembly 200 of forceps 10 (see FIG. 2A). Rather, in the storage condition, spatula-shaped energizable member 1120 extends to the distal end of or distally beyond proximal flanges 1014, 1024 of jaw members 1010, 1020 adjacent the proximal ends of jaw bodies 1011, 1021. Spatula-shaped energizable member 1120 is also offset relative to end effector assembly 1000, e.g., positioned above upper jaw member 1010 (as shown) or below lower jaw member 1120. As a result of this configuration, spatula-shaped energizable member 1120 does not extend beyond surface 1012 of jaw member 1010 (towards jaw member 1020) in either the spaced-apart position or the approximated position (see FIGS. 6A and 6B, respectively). Accordingly, spatula-shaped energizable member 1120 may be retained in a more-distal storage position as compared to energizable rod member 220 (FIG. 2A) without interfering with the use of jaw members 1010, 1020 for grasping, treating, and/or cutting tissue and without requiring an increased-diameter end effector assembly or insulative sleeve to accommodate spatula-shaped energizable member 1120. This more-distal storage position reduces the deployment distance required for deploying spatula-shaped energizable member 1120.

Referring to FIG. 6B, as monopolar assembly 1100 is transitioned towards the deployed condition, spatula-shaped energizable member 1120 is translated along jaw member 1010 and insulative sleeve 1110 is translated about end effector assembly 1000, ultimately reaching the deployed condition. In the deployed condition, as shown in FIG. 6C, insulative sleeve 1110 substantially surrounds end effector assembly 1000 and the distal end of spatula-shaped energizable member 1120 extends distally from end effector assembly 1000 and insulative sleeve 1110. In the deployed condition, spatula-shaped energizable member 1120 may be energized to treat tissue in a monopolar mode of operation. Further, spatula-shaped energizable member 1120 may be substantially retained between jaw member 1010 and insulative sleeve 1110 in the deployed position to inhibit movement thereof relative to end effector assembly 1000.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knives, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing;
an inner shaft coupled to and extending distally from the housing;
an end effector assembly disposed at a distal end of the inner shaft;
an outer sheath fixed to the housing and extending distally from the housing, the outer sheath disposed about the inner shaft;
an insulative sleeve positioned between the inner shaft and the outer sheath, the insulative sleeve movable relative to the inner shaft and the outer sheath between a storage position, wherein the insulative sleeve is positioned proximally of the end effector assembly, and a deployed position, wherein the insulative sleeve substantially surrounds the end effector assembly; and
an energizable member coupled to the insulative sleeve and movable in conjunction with the insulative sleeve between the storage position and the deployed position, wherein, in the deployed position, the energizable member extends distally from the insulative sleeve and the end effector assembly.

2. The surgical instrument according to claim 1, wherein the insulative sleeve and the inner shaft are rotatable in conjunction with one another and relative to the outer sheath and the housing.

3. The surgical instrument according to claim 1, wherein the insulative sleeve includes a proximal portion and a distal portion, the distal portion defining a diameter larger than that of the proximal portion to facilitate deployment of the insulative sleeve about the end effector assembly.

4. The surgical instrument according to claim 1, wherein the end effector assembly includes first and second jaw members configured to supply bipolar energy to tissue, and wherein the energizable member is configured to supply monopolar energy to tissue.

5. The surgical instrument according to claim 1, wherein the energizable member is positioned between the inner shaft and the outer sheath.

6. The surgical instrument according to claim 1, wherein a portion of the inner shaft extends distally from the outer sheath such that the end effector assembly is spaced apart from the outer sheath.

7. A surgical instrument, comprising: a housing; a shaft assembly extending distally from the housing and having an end effector assembly disposed at a distal end thereof, the shaft assembly including an insulative tube having a proximal portion extending distally from the housing and a distal portion extending distally from the proximal portion; and an insulative sleeve segment disposed about the distal portion of the insulative tube, the insulative sleeve segment movable about the distal portion of the insulative tube between a storage position, wherein the insulative sleeve segment is positioned adjacent the proximal portion of the insulative tube and proximally of the end effector assembly, and a deployed position, wherein the insulative sleeve segment is distally spaced apart from the proximal portion of the insulative tube and substantially surrounds the end effector assembly; wherein the proximal portion of the insulative tube partially overlaps the distal portion of the insulative tube to define a raised annular shoulder therebetween, wherein the insulative sleeve segment and raised annular shoulder define similar diameters, and wherein, in the storage position, the insulative sleeve segment is positioned adjacent the raised annular shoulder so as to form a continuous tubular body.

8. The surgical instrument according to claim 7, wherein the shaft assembly includes an outer shaft having the end effector disposed at a distal end thereof, the outer shaft disposed within and coupled to the insulative tube.

9. The surgical instrument according to claim 7, further including an energizable member coupled to the insulative sleeve segment and movable in conjunction with the insulative sleeve segment between the storage position and the deployed position, wherein, in the deployed position, the energizable member extends distally from the insulative sleeve segment and the end effector assembly.

10. The surgical instrument according to claim 9, wherein the energizable member is fixed relative to the insulative sleeve segment via at least one of a bonding ring or an insulative ferrule.

11. The surgical instrument according to claim 9, wherein the energizable member extends proximally through the shaft assembly and wherein a proximal end of the energizable member is coupled to a deployment mechanism configured to selectively deploy the energizable member and the insulative sleeve segment.

12. The surgical instrument according to claim 9, wherein the end effector assembly includes first and second jaw members configured to supply bipolar energy to tissue, and wherein the energizable member is configured to supply monopolar energy to tissue.

* * * * *